Figure 1:
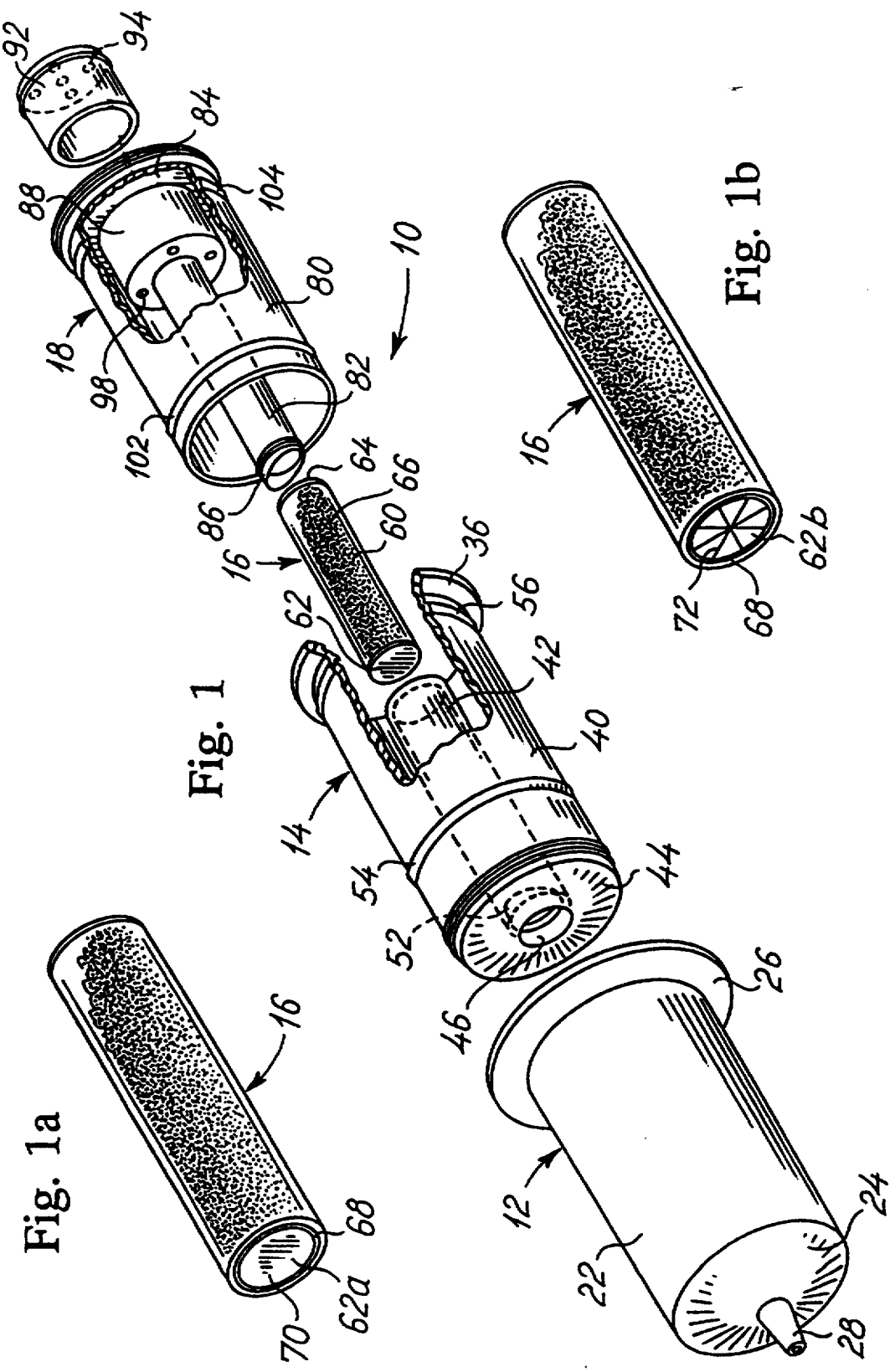

United States Patent [19]

Morris

[11] Patent Number: 5,429,603
[45] Date of Patent: Jul. 4, 1995

[54] TWO-COMPARTMENT SYRINGE ASSEMBLY AND A METHOD OF PRODUCING A TWO-COMPARTMENT SYRINGE ASSEMBLY

[75] Inventor: Michael Morris, Varde, Denmark
[73] Assignee: Medinject A/S, Birkeroed, Denmark
[21] Appl. No.: 781,220
[22] PCT Filed: Dec. 4, 1991
[86] PCT No.: PCT/DK91/00380
    § 371 Date: Jan. 2, 1992
    § 102(e) Date: Jan. 2, 1992
[87] PCT Pub. No.: WO92/10225
    PCT Pub. Date: Jun. 25, 1992

[30] Foreign Application Priority Data
Dec. 4, 1990 [DK] Denmark .............. 2885/90

[51] Int. Cl.$^6$ .............. A61M 37/00
[52] U.S. Cl. .............. 604/88; 604/87; 604/89
[58] Field of Search .............. 604/82-93, 604/194-199, 218, 221, 222, 231-232, 139, 148, 200-205, 226, 235, 244-246, 411-416, 183, 184; 433/80, 89

[56] References Cited

U.S. PATENT DOCUMENTS

| | | |
|---|---|---|
| 1,503,219 | 7/1924 | Wedig .............. 604/226 |
| 2,778,360 | 1/1957 | Miskel .............. 604/87 |
| 3,108,591 | 10/1963 | Kolbas . |
| 3,327,710 | 6/1967 | Freeberg et al. . |
| 3,477,432 | 11/1969 | Shaw .............. 604/91 |
| 3,557,787 | 1/1971 | Cohen .............. 604/90 |
| 3,570,486 | 3/1971 | Engelsher . |
| 3,595,439 | 7/1971 | Newby .............. 222/80 |
| 3,685,514 | 8/1972 | Cheney . |
| 3,890,971 | 6/1975 | Leeson et al. . |
| 4,254,768 | 3/1981 | Ty . |
| 4,306,554 | 12/1981 | Schwartz et al. . |
| 4,464,174 | 8/1984 | Ennis . |
| 4,546,767 | 10/1985 | Smith . |
| 4,693,706 | 9/1987 | Ennis, III . |
| 4,768,568 | 9/1988 | Fournier et al. . |
| 4,886,495 | 12/1989 | Reynolds . |
| 4,910,259 | 3/1990 | Kindt-Larsen et al. . |

FOREIGN PATENT DOCUMENTS

| | | |
|---|---|---|
| 0397589 | 11/1990 | European Pat. Off. . |
| 1164351 | 10/1958 | France . |
| 2838222 | 3/1980 | Germany . |
| 3618318 | 3/1987 | Germany . |
| 7102491 | 8/1975 | Sweden . |
| 464797 | 6/1991 | Sweden . |
| 622752 | 4/1981 | Switzerland . |
| 1313339 | 4/1973 | United Kingdom . |
| 1413734 | 11/1975 | United Kingdom . |
| 85/04567 | 10/1985 | WIPO . |
| 86/06618 | 11/1986 | WIPO . |

OTHER PUBLICATIONS

Copy of database search in the name of Kabi Pharmac identifying patent applications and patents filed in the name of Kabi Pharmacia AB which is a Swedish Company.

*Primary Examiner*—C. Fred Rosenbaum
*Assistant Examiner*—V. Alexander
*Attorney, Agent, or Firm*—Merchant & Gould, Smith, Edell, Welter & Schmidt

[57] ABSTRACT

A two-compartment syringe assembly (10) is composed of a first, outer cylindrical barrel (12), a second, inner cylindrical barrel (14) in which a material (66) is enclosed within a capsule part or ampulla (16) which is received and protected within the second cylindrical barrel, a plunger (18) and a liquid (20), which is enclosed within a first compartment defined within the first cylindrical barrel (12). As the material is concealed within the second cylindrical barrel, any risk of leakage of the material to the environment or atmosphere in case the two-compartment syringe assembly is exposed to shocks, such as mechanical blows, is radically reduced as compared to conventional two-compartment syringe assemblies. Furthermore, any toxic aerosols and gases generated as the material (66) is dispensed from the ampulla (16) to the first compartment containing the liquid (20) are vented through an activated carbon filling (90) of a central plunger body (82) of the plunger (18), which plunger body serves the purpose of dispensing the material (66) from the ampulla (16) as the two-compartment syringe assembly is operated.

21 Claims, 4 Drawing Sheets

Fig. 2
Fig. 3
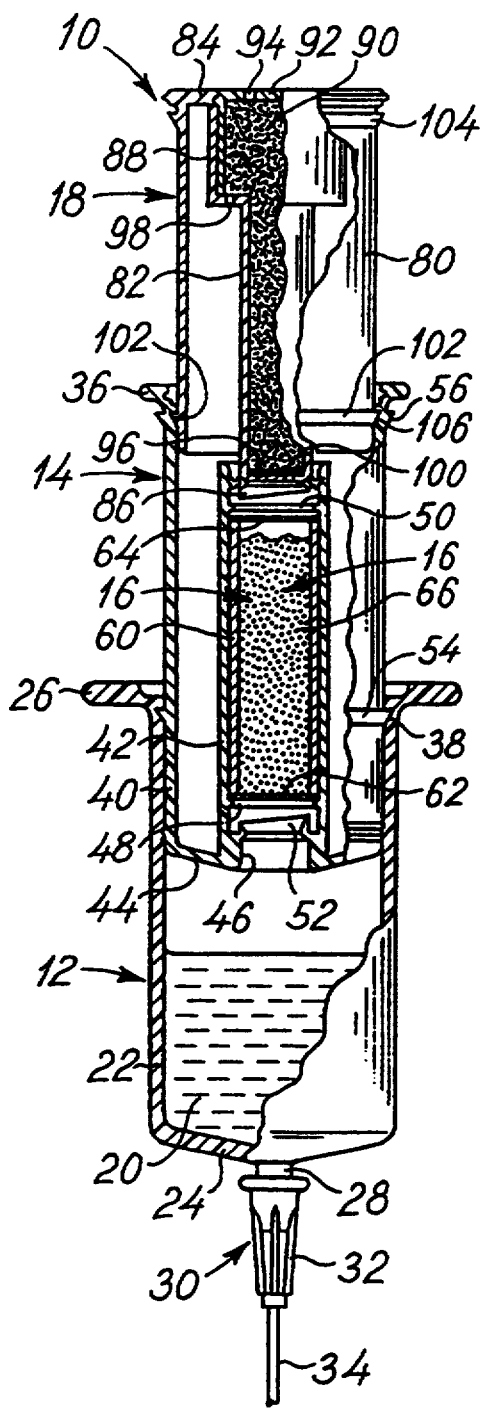
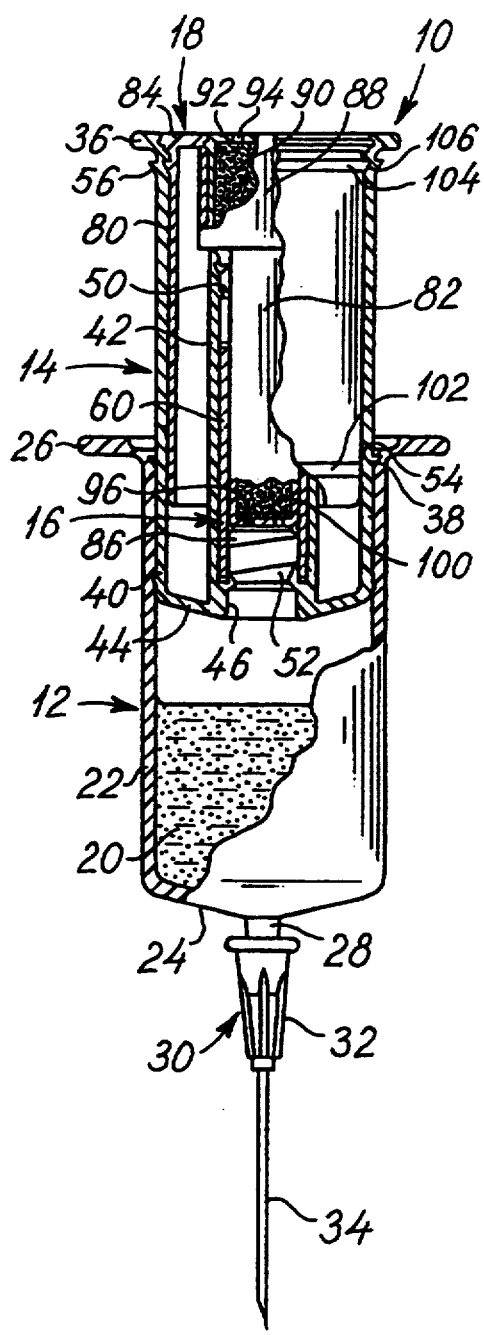

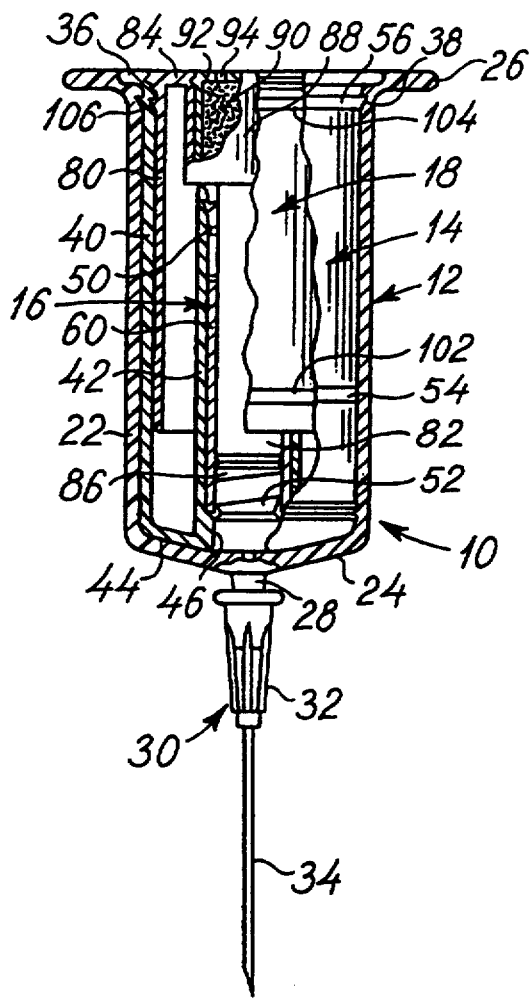
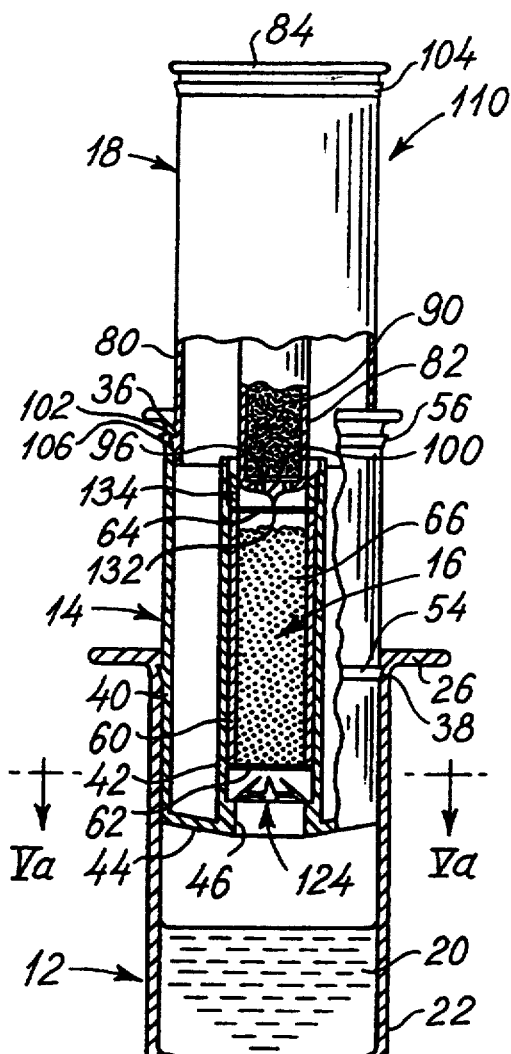
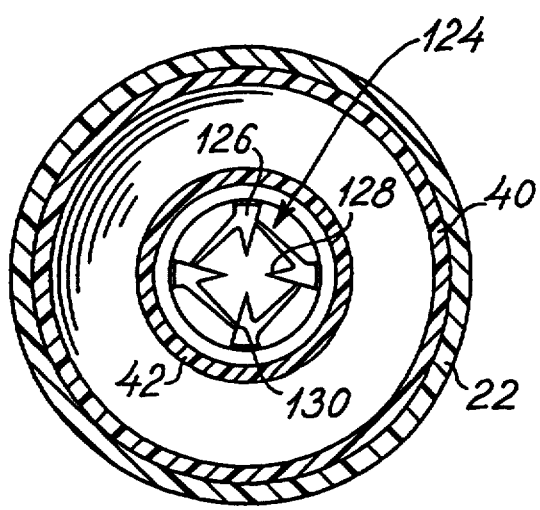
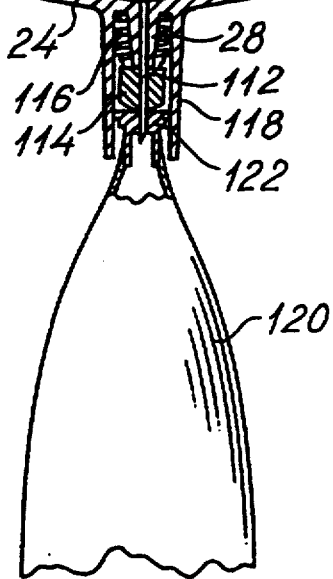

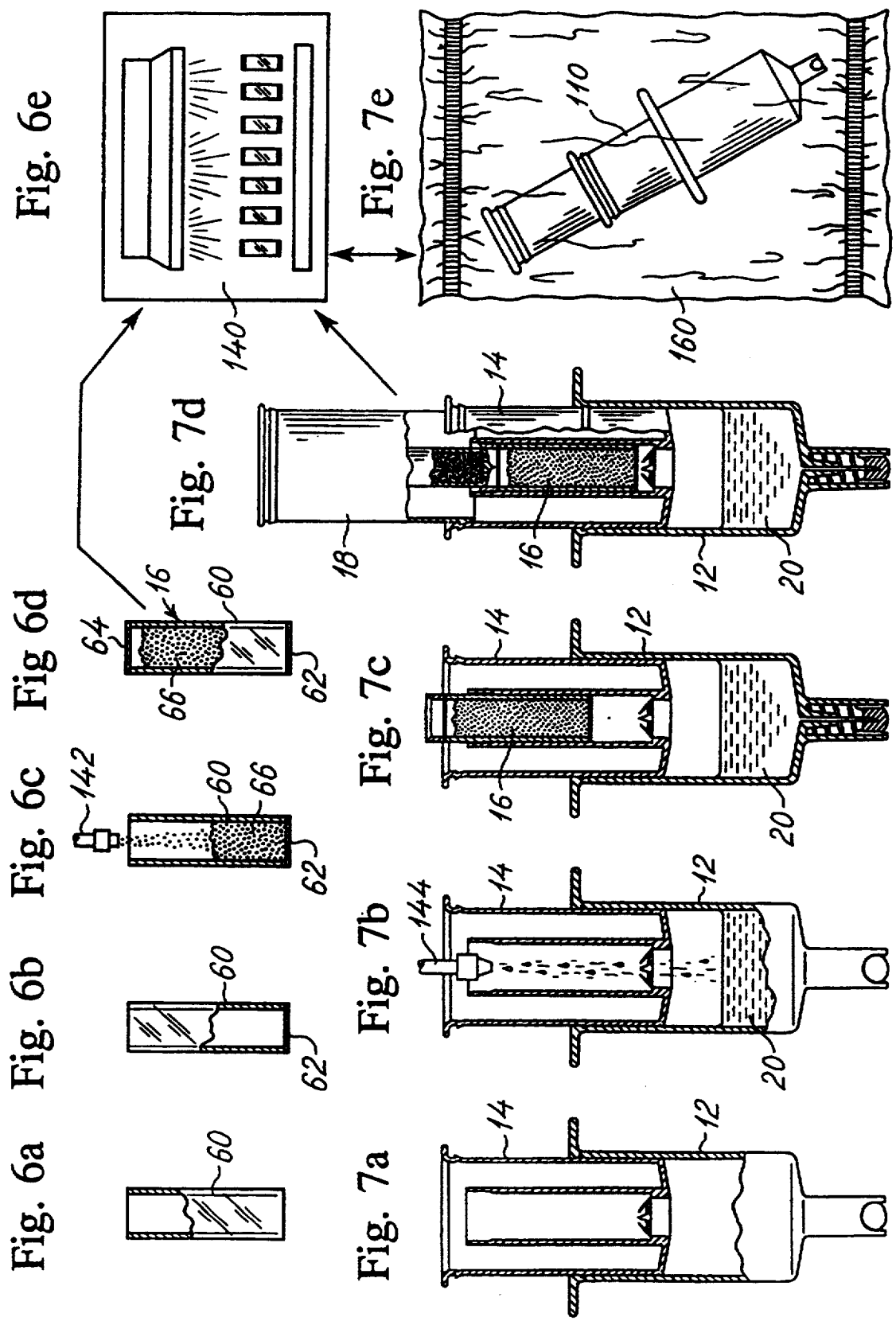

TWO-COMPARTMENT SYRINGE ASSEMBLY AND A METHOD OF PRODUCING A TWO-COMPARTMENT SYRINGE ASSEMBLY

The present invention relates to a two-compartment syringe assembly for storing a liquid and a material, and for preparing a dilution of said material within said liquid prior to dispensing said liquid, and further to a method of producing a two-compartment syringe assembly for storing a liquid and a material and for preparing a dilution of said material within said liquid prior to dispensing said liquid.

From published European Patent Application, Publication No. 0397589, an apparatus for preparing a mixture of a solid, particulate or powdered component, and a liquid component, so as to provide a paste-like material therefrom is known, particularly for preparing acrylate bone cement. U.S. Pat. No. 4,910,259 describes an acrylate bone cement which is preferably used in the apparatus known from the published European patent application.

The technique of storing two components such as a liquid or solvent and a material, such as a medicament constituting a solid or liquid component within separate containers or barrels of a so-called two-compartment syringe prior to preparing a dilution of the material within the liquid is also well-known within the art. Reference is to be made to CH 622752, GB 1313339, GB 1413734, DE 2838222, WO 85/04567, WO 86/06618, FR 1164351, SE 378064, SE 464797, U.S. Pat. No. 3,108,591, U.S. Pat. No. 3,570,486, U.S. Pat. No. 3,685,514, U.S. Pat. No. 4,254,768, U.S. Pat. No. 4,306,554, U.S. Pat. No. 4,464,174, U.S. Pat. No. 4,546,767, U.S. Pat. No. 4,693,706, U.S. Pat. No. 4,768,568, and U.S. Pat. No. 4,886,495, and the above-listed U.S. patents are further incorporated in the present specification by reference.

A representative example of the prior art two-compartment syringe assembly is disclosed in U.S. Pat. No. 3,685,514 which two-compartment syringe assembly is basically composed of two separate, conventional syringes, one of which constitutes an inner syringe comprising an inner barrel and a plunger, which inner barrel contains the liquid or solvent. The inner barrel and plunger together constitute a plunger assembly of an outer syringe which further comprises an outer barrel containing the medicament. Among the above-listed references, elaborated structures comprising sealed capsules to be perforated and elaborated vents are disclosed.

Common to the two-compartment syringe assemblies known within the art is the fact that the active material, i.e. the medicament or an active liquid component which is to be diluted within the liquid prior to dispensing from the two-compartment syringe assembly is contained within the outer barrel.

A serious drawback of the two-compartment syringe assembly is due to the lack of providing a controllable venting of the two-compartment syringe assembly when the dilution is prepared, as some materials or medicaments when diluted in a liquid or in a solvent create aerosols and gases which have to be vented, however, have to be vented through filtering means in order to eliminate to any substantial extent the risk that the person, such as a doctor, a nurse, or a pharmacist, operating the two-compartment syringe assembly is exposed to hazardous, such as toxic or carcinogenic aerosols and gases.

Particularly when preparing cytostatics, serious problems have arisen, since hazardous, such as toxic or carcinogenic aerosols and gases are developed. Hitherto, attempts have been made as to solving these serious problems by prescribing that the person operating the two-compartment syringe assembly should use gloves, masks, specialized semi-closed mixing devices and carry out the mixing or preparation procedure in a fume cupboard with forced ventilation.

A further drawback of the two-compartment syringe assembly originates from the fact that the two-compartment syringe assembly in case it is exposed to shocks or blows or dropped on a floor may leak, causing an extremely hazardous situation in case the two-compartment syringe assembly is dropped, e.g. in a hospital.

An object of the present invention is to provide a two-compartment syringe assembly for storing a liquid and a material such as a powder medicament or an active liquid component and for preparing a dilution of the material within the liquid prior to dispensing the liquid from the two-compartment syringe assembly which syringe assembly provides a radically improved protection of the staff producing the two-compartment syringe assembly, handling the two-compartment syringe assembly while transferring the two-compartment syringe assembly from the manufacturing plant to the hospital and operating the two-compartment syringe assembly for preparing the dilution prior to dispensing the dilution of the material within the liquid, as the two-compartment syringe assembly provides a mechanical protection of the container in which the material is enclosed in a sealed compartment eliminating to any substantial extent the risk that the material, i.e. the active material, such as cytostatics, leaks to the environment in case an outer component such as a wall of the two-compartment syringe assembly is broken.

A particular feature of the two-compartment syringe assembly originates from the fact that the two-compartment syringe assembly is easily constructed so as to provide a controlled venting of the two-compartment syringe assembly by providing a separate venting channel in which a filtering means is enclosed, e.g. comprising activated carbon.

A particular advantage of the two-compartment syringe assembly according to the present invention relates to the provision of a separate sealed ampulla enclosing the material, such as the active liquid component or the medicament, e.g. a cytostatic, which ampulla is received within the two-compartment syringe assembly fulfilling the above object as the ampulla is concealed within the two-compartment syringe assembly and protected from being damaged by shocks or blows, e.g. in case the two-compartment syringe assembly is dropped.

The above object, the above feature, and the above advantage, together with numerous other objects, features, and advantages are obtained by means of a two-compartment syringe assembly for storing a liquid and a material and for preparing a dilution of the material within the liquid prior to dispensing the liquid, comprising:

a first cylindrical barrel having a first cylindrical wall and defining a first and a second end of the first cylindrical barrel, a first compartment being defined within the first cylindrical barrel by the first cylindrical wall, the first end of the first cylindrical barrel constituting a dispensing end and the second end of the first cylindrical barrel being open, a second cylindrical barrel having an outer cylindrical wall, an inner cylindrical wall, and an end wall and defining a first and a second end of the second cylindrical barrel, the outer and inner cylindrical walls being integrally connected through the end wall at the first end of the second cylindrical barrel, a second compartment being defined within the second cylindrical barrel by the inner cylindrical wall of the second cylindrical barrel and constituting a sealed compartment sealed by rupturable seals provided at the first and second ends of the second cylindrical barrel, a plunger having a central plunger body and an outer peripheral plunger wall circumferentially encircling the central plunger body, the liquid being received within the first compartment of the first cylindrical barrel, and the material being enclosed within the second compartment of the second cylindrical barrel, the plunger being inserted into the second cylindrical barrel through the second end thereof, having its plunger body registered relative to the inner cylindrical wall of the second cylindrical barrel, and having its outer peripheral plunger wall received within the outer cylindrical wall of the second cylindrical barrel, the plunger being axially displaceable relative to the second cylindrical barrel from a first, extracted position to a second, inserted position in which the plunger body of the plunger is inserted into the second compartment of the second cylindrical barrel through the second end thereof, having ruptured the rupturable seals at the first and second ends of the second cylindrical barrel, and establishes a sealing relationship with the inner cylindrical wall of the second cylindrical barrel, so as to allow the material to be dispensed from the second compartment to the first compartment for being diluted within the liquid, the second cylindrical barrel being inserted into the first cylindrical barrel through the second end thereof, having its first end received within the first compartment, the second cylindrical barrel being axially displaceable relative to the first cylindrical barrel in sealing relationship therewith from a third, extracted position to a fourth position in which the first compartment is substantially diminished and the liquid is dispensed from the first cylindrical barrel through the first end thereof.

As the material is enclosed within the second compartment of the second cylindrical barrel, i.e. enclosed within the inner cylindrical wall of the second cylindrical barrel concealed behind the outer cylindrical wall of the second cylindrical barrel, the risk of leakage from the second compartment containing the material to the atmosphere or environment in case the two-compartment syringe assembly is exposed to shocks or blows, is radically reduced as compared to the prior art two-compartment syringe assemblies in which the material is enclosed within the outer barrel of the structure, i.e. within the barrel corresponding to the first cylindrical barrel of the two-compartment syringe assembly according to the present invention.

Furthermore, as the liquid is received within the first compartment of the first cylindrical barrel and enclosed within the first compartment, any risk of evaporation of the liquid from the first compartment, and consequently from the two-compartment syringe assembly according to the present invention to the environment is eliminated, and any risk of contamination of the liquid from the environment is also eliminated due to the enclosing of the liquid within the first compartment of the two-compartment syringe assembly according to the present invention.

According to the presently preferred embodiment of the two-compartment syringe assembly acccording to the present invention, the plunger defines a venting passage extending through the plunger body, in which venting passage a filtering means is enclosed. The filtering means preferably comprises a hydrophobic filter means, such as a foil or membrane of micropore polyurethane (PU), micropore polytetrafluoroethylene (PTFE), micropore polypropylene (PP), micropore polyethylene (PE), polytrimethylsilylpropylene or polydimethylsiloxane, a micropore fibre filter, and an activated carbon filter body. Thus, any hazardous, such as carcinogenic or toxic aerosols and/or gases produced as the material is diluted within the liquid is vented through the activated carbon filter body, and any risk of exposing the person, such as the doctor, the nurse, or the pharmacist operating the two-compartment syringe assembly, is to any substantial extent eliminated or at least radically reduced as compared to the prior art two-compartment syringe assemblies.

The filtering means enclosed within the plunger body of the plunger of the two-compartment syringe assembly according to the present invention may in accordance with an alternative embodiment comprise a foil of a material which is soluble in the liquid contained within the first compartment of the two-compartment syringe assembly. Thus, provided the liquid contains water, e.g. in an aqueous solution of NaCl, the soluble material may be polyvinyl alcohol of a foil of a thickness of e.g. 10–20 $\mu$m. The liquid-soluble foil is preferably arranged as a first barrier of the filter means separating the remaining components of the filtering means, such as the hydrophobic filter means, the micropore fibre filter, and the activated carbon filter body from the first and second compartment of the two-compartment syringe assembly. By providing a liquid-soluble foil, the rupturable seals provided at the first and second ends of the second cylindrical barrel is easily perforated as the second rupturable seal is first perforated as the plunger is advanced from its first, extracted position relative to the second cylindrical barrel of the two-compartment syringe assembly towards the second, inserted position relative to the second cylindrical barrel of the two-compartment syringe assembly. After the second rupturable seal is ruptured, the liquid-soluble foil of the filter means provides a sealing membrane which consequently seals the second compartment relative to the environment which causes a compression of the air enclosed within the second compartment as the plunger is further advanced, which increase in gas pressure within the second compartment as the plunger is further advanced eventually perforates or ruptures the rupturable seal at the first end of the second cylindrical barrel so as to allow the material to be dispensed from the second compartment to the first compartment and so as to expose the liquid-soluble foil to the liquid for dissolving at least part of the liquid-soluble foil and for allowing that aerosols and/or gases are vented from the first compartment through the filtering means to the atmosphere. Provided the liquid is a non-aqueous liquid, a different soluble foil material has to be provided. Also, the material has to be enclosed within the second compartment of the second cylindrical barrel in non-evacuated state, e.g. in a gas which is inert or inactive relative to the material, such as for most materials nitrogen, or an inert gas such as e.g. argon.

In order to guarantee that the two-compartment syringe assembly is not disassembled, e.g. prior to the preparation of the dilution of the material within the liquid or after the preparation and after the dispensing of the liquid containing the material dilution, the two-compartment syringe assembly preferably further comprises separate locking means for locking the first cylindrical barrel, the second cylindrical barrel, and the plunger in specific positions and for blocking the cylindrical barrels and the plunger from being disassembled.

More specifically, the two-compartment syringe assembly preferably further comprises a first, breakable locking means for locking the plunger in the first, extracted position relative to the second cylindrical barrel, however, allowing, when broken, that the plunger is displaced relative to the second cylindrical barrel from the first, extracted position to the second, inserted position, and preferably further comprises a second locking means for locking the plunger in the second, inserted position relative to the second cylindrical barrel when displaced to the second, inserted position from the first, extracted position and for preventing the plunger from being retracted from the second, inserted position relative to the second cylindrical barrel. The two-compartment syringe assembly according to the present invention preferably further comprises a third, breakable locking means for locking the second cylindrical barrel in the third, extracted position relative to the first cylindrical barrel, however, allowing, when broken, that the second cylindrical barrel is displaced relative to the first cylindrical barrel from the third, extracted position to the fourth position, and preferably further comprises a fourth locking means for locking the second cylindrical barrel in the fourth position relative to the first cylindrical barrel when displaced to the fourth position from the third, extracted position and for preventing the second cylindrical barrel from being retracted from the fourth position relative to the first cylindrical barrel.

The first and second cylindrical barrels and the plunger of the two-compartment syringe assembly according to the present invention may be made from any appropriate material, such as a thermoplastic material, e.g. polystyrene, polyimide, polycarbonate, polymethacrylates, polyvinylidenefluoride, polyamide, polyvinyl alcohol, and preferably polyolefines, such as low-density polyethylene (LDPE), medium-density polyethylene (MDPE), high-density polyethylene (HDPE), linear low-density polyethylene (LLDPE), polypropylene (PP), polypropylene-ethylene-copolymer, or any mixture thereof.

Provided the material contained within the second compartment defined within the second cylindrical barrel by the inner cylindrical wall thereof is an aggressive material which may decompose or degrade the material of the inner cylindrical wall of the second cylindrical barrel, e.g. provided the second cylindrical barrel is made from one of the above-listed materials, the inner cylindrical wall of the second cylindrical barrel may preferably be made from a material which has been surface-treated in order to provide barrier properties by electron-ray-treatment, corona-treatment, plasma-treatment, plasma-polymerisation or any other appropriate surface-treatment.

According to a particular feature of the present invention, the material is in accordance with the presently preferred embodiment of the two-compartment syringe assembly according to the present invention contained in a separate capsule or ampulla which on the one hand may be manufactured in a conventional production plant and on the other hand may easily be made from a material such as glass, which may stand exposure to active or aggressive materials such as cytostatics or the like. Consequently, in accordance with the presently preferred embodiment of the two-compartment syringe assembly according to the present invention, the second cylindrical barrel is composed of an outer body part and a capsule part, the capsule part comprising the inner cylindrical wall and the rupturable seals, and the outer body part constituting a support structure having a central recess in which the capsule part is received. Advantageously, the capsule part constitutes a prefilled, sterilized ampulla, and the capsule part preferably comprises a cylindrical glass tube having opposite ends in which the rupturable seals are fixated relative to the cylindrical glass tube. However, the capsule part may be made from any other appropriate material, such as a plastic material, e.g. the thermoplastic materials mentioned above which may further be surface-treated as discussed above.

The rupturable seals of the second cylindrical barrel or, additionally or alternatively, of the separate capsule part of the second cylindrical barrel optionally constituting a prefilled, sterilized ampulla may be made from any appropriate resistent and gas-impermeable material, such as a foil of a thermoplastic material, e.g. a foil of LDPE, LLDPE, MDPE, HDPE, PP, PU, polyvinyl alcohol, polyimide, polyamide, polyvinylidenefluoride, cellulose acetate, polyvinyl acetate, copolymers and laminates thereof, a foil of aluminum, or a laminated multilayer combination thereof.

The two-compartment syringe assembly may be used for storing and preparing any material such as a powdered or particulate material or a viscous material such as a liquid, which material is to be diluted in a liquid such as a solvent prior to dispensing the liquid having the material diluted therein from the two-compartment syringe assembly. The material may be any organic or inorganic material to be stored in a separate compartment, i.e. within the second compartment of the second cylindrical barrel of the two-compartment syringe assembly according to the present invention. Similarly, the liquid may constitute any organic or inorganic liquid, such as a solvent, an alcoholic or aqueous solution, a base, an acid, a saline or sugary solution or the like, or any combination thereof. The material, however, preferably constitutes a highly active or aggressive material, such as pharmaceuticals, e.g. cytostatics, anti-biotics, hormones, central nervous agents, vaccines, anti-dotes, anti-bodies, anti-allergic agents, anti-coagulants, analgesics, aggressive solutions, such as acids, bases, electrolyte solutions, solvents, such as DMSO (dimethylenesulphoxide) or any other materials or medicaments to be stored in a separate container, e.g. in a non-aqueous environment or in a highly concentrated solution.

In order to render it easier for the person operating the two-compartment syringe assembly according to the present invention to perforate the rupturable seals of the second cylindrical barrel of the two-compartment syringe assembly, the two-compartment syringe assembly according to the present invention preferably further comprises a first seal-breaking means provided at the first end of the second cylindrical barrel for breaking the rupturable seal at the first end of the second cylindrical barrel when the plunger is displaced axially relative to the second cylindrical barrel from the first, extracted position towards the second, inserted position and further preferably comprises a second seal-breaking means provided at the plunger body of the plunger for breaking the rupturable seal at the second end of the second cylindrical barrel when the plunger is displaced axially relative to the second cylindrical barrel from the first, extracted position towards the second, inserted position.

Provided the second cylindrical barrel of the two-compartment syringe assembly according to the present invention is implemented in accordance with the above-described, presently preferred embodiment as a composition of an outer body part and a capsule part, the first seal-breaking means may be constituted by a cutting means provided at the support structure for perforating the rupturable seal as the capsule part is displaced within the central recess of the outer body part from a fifth, retracted position in which the rupturable seal provided at the first end of the second cylindrical barrel is out of contact with the first seal-breaking means and into a sixth position in which the rupturable seal provided at the first end of the second cylindrical barrel is brought into contact with the first seal-breaking means through impact from the plunger agitating the capsule part.

The present invention also relates to a method of producing a two-compartment syringe assembly for storing a liquid and a material and for preparing a dilution of the material within the liquid prior to dispensing the liquid, and more specifically a method of producing a two-compartment syringe assembly according to the present invention. Consequently, the method according to the present invention comprises the steps of:

providing a first cylindrical barrel having a first cylindrical wall and defining a first and a second end of the first cylindrical barrel, a first compartment being defined within the first cylindrical barrel by the first cylindrical wall, the first end of the first cylindrical barrel constituting a dispensing end and the second end of the first cylindrical barrel being open, providing a second cylindrical barrel having an outer cylindrical wall, an inner cylindrical wall, and an end wall and defining a first and a second end of the second cylindrical barrel, the outer and inner cylindrical walls being integrally connected through the end wall at the first end of the second cylindrical barrel, a second compartment being defined within the second cylindrical barrel by the inner cylindrical wall of the second cylindrical barrel and constituting a sealed compartment sealed by rupturable seals provided at the first and second ends of the second cylindrical barrel, providing a plunger having a central plunger body and an outer peripheral plunger wall circumferentially encircling the central plunger body, arranging the liquid being received within the first compartment of the first cylindrical barrel, arranging the material being enclosed within the second compartment of the second cylindrical barrel, inserting the plunger into the second cylindrical barrel through the second end thereof, having its plunger body registered relative to the inner cylindrical wall of the second cylindrical barrel, and having its outer peripheral plunger wall received within the outer cylindrical wall of the second cylindrical barrel, so that the plunger is axially displaceable relative to the second cylindrical barrel from a first, extracted position to a second, inserted position in which the plunger body of the plunger is inserted into the second compartment of the second cylindrical barrel through the second end thereof, having ruptured the rupturable seals at the first and second ends of the second cylindrical barrel, and establishes a sealing relationship with the inner cylindrical wall of the second cylindrical barrel, so as to allow the material to be dispensed from the second compartment to the first compartment for being diluted within the liquid, and inserting the second cylindrical barrel into the first cylindrical barrel through the second end thereof, having its first end received within the first compartment, so that the second cylindrical barrel is axially displaceable relative to the first cylindrical barrel in sealing relationship therewith from a third, extracted position to a fourth position in which the first compartment is substantially diminished and liquid is dispensed from the first cylindrical barrel through the first end thereof.

The method according to the present invention is preferably implemented for producing the above-described, presently preferred embodiment of the two-compartment syringe assembly according to the present invention, and consequently preferably comprises the introductory step of producing the second cylindrical barrel as a combination of an outer body part and a capsule part, the capsule part comprising the inner cylindrical wall and the rupturable seals, and the outer body part constituting a support structure having a central recess in which the capsule part is received, and of arranging the material enclosed within the capsule part.

The present invention will now be further described with reference to the drawings, in which FIG. 1 is an exploded and perspective view of a first, presently preferred embodiment of a two-compartment syringe assembly according to the present invention comprising a separate medicament-containing ampulla, FIGS. 1a and 1b are perspective views of alternative embodiments of the medicament-containing ampulla to be used in the two-compartment syringe assembly according to the present invention, FIGS. 2–4 are schematic and sectional views of the first, presently preferred embodiment of the two-compartment syringe assembly according to the present invention illustrating separate steps of operating the two-compartment syringe assembly for preparing a dilution of a medicament contained within the two-compartment syringe assembly within a diluting liquid or solvent also contained within the two-compartment syringe assembly, FIG. 5 is a schematic and sectional view corresponding to the view of FIG. 2 of a second, slightly modified embodiment of the two-compartment syringe assembly according to the present invention, FIG. 5a is a perspective view of a membrane-perforating or cutting means of the second embodiment of the two-compartment syringe assembly shown in FIG. 5, FIGS. 6a–6e are schematic views illustrating a method of filling the ampulla of the two-compartment syringe assembly according to the present invention, and FIGS. 7a–7e are schematic views illustrating a method of filling and sealing the two-compartment syringe assembly according to the present invention.

In FIGS. 1–4, a first, presently preferred embodiment of a two-compartment syringe assembly is shown for storing a liquid and a material, such as a medicament, and for preparing a dilution of the material or medicament within the liquid prior to dispensing the liquid from the two-compartment syringe assembly. The two-compartment syringe assembly is in its entirety designated the reference numeral 10. Basically, the two-compartment syringe assembly 10 is composed of a total of four separate components or parts, viz. a first or outer cylindrical barrel 12, a second or inner cylindrical barrel 14, a material or medicament-containing ampulla 16, and a plunger 18. The ampulla 16 is received within the second or inner cylindrical barrel 14, as will be described in greater details below.

The first cylindrical barrel 12 constitutes a main barrel of the two-compartment syringe assembly, in which barrel the diluting liquid is contained and in which barrel the process of preparing a dilution of the medicament within the diluting liquid is performed. The liquid is shown in FIG. 2 and is designated the reference numeral 20.

The first cylindrical barrel 12 comprises a cylindrical wall 22 defining a first end or dispensing end 24 and an opposite, open end at which a circumferential flange 26 extends radially outwards from the cylindrical wall 22. At the center of the first end or dispensing end 24, a spout or nozzle 28 is provided. At the spout or nozzle 28, a needle assembly 30 is mounted, comprising a fixation component 32 co-operating with the spout or nozzle 28, and an elongated needle 34 extending from the distal end of the fixation component 32.

The second or inner cylindrical barrel 14 constitutes a support structure in which the medicament-containing ampulla 16 is received. The inner cylindrical barrel 14 basically comprises an outer cylindrical wall 40, an inner cylindrical wall 42 and an end wall 44 which is arranged at a first end of the inner cylindrical barrel 14 interconnecting the outer and inner cylindrical walls 40 and 42, respectively.

The end wall 44 is provided with a central through-going hole 46 which is arranged in registration with an inner space defined within the inner cylindrical wall 42, in which inner space the ampulla 16 is received. The ampulla 16 is, as is evident from FIG. 2, supported in a storage position within the inner space defined within the inner cylindrical wall 42 and is restricted from moving axially within the inner space relative to the inner cylindrical barrel 14 by inwardly protruding, annular projections 48 and 50.

A cutter means 52 of an annular configuration and constituting a separate component received within and supported by the inner cylindrical barrel 14 is arranged recessed relative to the end wall 44 thereof at the central, through-going hole 46 serving the purpose of perforating the ampulla 16 as the ampulla is displaced axially beyond the inwardly protruding, annular projection 48, as will be described in greater details below.

The end wall 44 defines a first end of the inner cylindrical barrel 14, the opposite, second end of which is open.

At the open, second end of the inner cylindrical barrel 14, an outwardly protruding, annular flange 36 is provided. From the outer surface of the outer cylindrical wall 40 of the inner cylindrical barrel 14, two outwardly protruding, annular projections 54 and 56 extend, which annular projections co-operate with a circumferential recess 38 provided at the inner surface of the cylindrical wall 22 of the outer cylindrical barrel 12 at the second, open end thereof.

The ampulla 16 basically comprises a cylindrical glass tube 60 having opposite first and second ends at which rupturable sealing membranes 62 and 64, respectively, are provided. Within the sealed inner compartment defined within the cylindrical glass tube 60 of the ampulla 16, the material or medicament to be diluted within the liquid 20 and later on dispensed from the two-compartment syringe assembly 60 is enclosed.

FIG. 1a and FIG. 1b disclose in greater details two alternative embodiments of the ampulla 16. The alternative embodiments of the ampulla 16 shown in FIG. 1a and 1b basically differ from one another and from the embodiment shown in FIG. 1 in that the rupturable sealing membranes shown in FIG. 1 and 1b designated the reference numerals 62a and 62b, respectively, are provided with score lines for reducing the pressure or force required for perforating the ampulla.

In FIG. 1a, the rupturable sealing membrane 62a is provided with a circumferential score line 68 defining a central, circular membrane segment 70 which is easily, i.e. at low pressure or low force, separated from the rest of the ampulla 16 along the score line 68.

In FIG. 1b, a total of six radially extending score lines are provided extending from the center of the rupturable, sealing membrane 62b to the circumferential score line 68. One of the radially extending score lines is designated the reference numeral 72. Preferably, the radial score lines 72 are more easily ruptured than the circumferential score line 68 shown in FIG. 1b in order to eliminate any risk that separate membrane segments of the rupturable, sealing membrane 62b is separated from the ampulla 66 as the ampulla is perforated along the score lines 72.

Obviously, the rupturable, sealing membranes provided at the opposite first and second end of the ampulla 16 may be of identical configuration or alternatively of different configuration. Thus, one of the membranes, or both membranes, may be provided with score lines, and the score lines of the two membranes may even be different from one another.

The plunger 18 basically constitutes a piston component relative to the inner cylindrical barrel 14 serving the main purpose of dispensing the material or medicament 66 from the ampulla 16 to the liquid 20 of the outer cylindrical barrel 12, as will be described in greater details below with reference to FIG. 3.

The plunger 18 comprises an outer peripheral plunger wall 80, a central plunger body 82, and an end wall 84. The plunger body 82 extends beyond the outer peripheral rim of the outer peripheral plunger wall 80 at a first end of the plunger 18, whereas the end wall 84 is provided at an opposite, second end of the plunger interconnecting the outer peripheral plunger wall 80 and the plunger body 82. At the outer, exposed end of the plunger body 82, a cutter means 86 is provided, which cutter means 86 basically corresponds to the cutter means 52 of the inner cylindrical barrel 14.

The plunger body 82 is of a basically hollow configuration and is at its upper end opposite to the cutter means 86 provided with a filter container 88. Within the plunger body 82 and the filter container 88, a filtering means such as activated carbon is enclosed, as is evident from FIGS. 2-4. The activated carbon-filling of the innerspace defined within the plunger body 82 and the filter container 88 is designated the reference numeral 90.

A plug body 92 seals the interior of the plunger body 82 and the filter container 88, which plug body comprises a plane outer surface through which venting holes are provided. One of the venting holes is designated the reference numeral 94. At the lower end of the plunger body 82, through-going holes are provided, one of which is designated the reference numeral 96, and a plurality of through-going holes are also provided at a radial surface of the filter container 88, one of which is designated the reference numeral 98.

A hydrophobic filter, such as a foil of micropore polyurethane or micropore polytetrafluorethylene, and optionally combined with a micropore fibre filter designated the reference numeral 100 in its entirety is also inserted within the inner space defined within the plunger body 82 at the lower end thereof, serving the purpose of blocking water and microparticles from being transmitted through the combined hydrophobic filter and micropore fibre filter 100 and further through the activated carbon-filling 90 to the environment from the innerspaces defined within the two-compartment syringe assembly 10 during the process of transferring the material or medicament 66 from the ampulla 16 to the liquid 20 of the outer cylindrical barrel 12 and of preparing a dilution of the material or medicament in the liquid and thereupon of dispensing the dilution from the two-compartment syringe assembly, as will be described in greater details with reference to FIGS. 2-4. Like the inner cylindrical barrel 14, the plunger 18 is also provided with two outwardly protruding, annular projections 102 and 104 co-operating with a circumferential recess 106 of the inner surface of the outer cylindrical wall 40 of the inner cylindrical barrel 14.

In FIG. 2, the two-compartment syringe assembly 10 is shown in a state ready for use. In this state, the inner cylindrical barrel 14 is received within the outer cylindrical barrel 12 as the first end of the inner cylindrical barrel 14 is inserted through the second, open end of the outer cylindrical barrel 12 and is locked in an extracted position as the outwardly protruding, annular projection 54 is received within the recess 38, preventing the inner cylindrical barrel 14 from being retracted from the outer cylindrical barrel 12. The dovetail-like engagement of the projection 54 within the recess 38, however, allows that the inner cylindrical barrel 14 may be advanced into the innerspace defined within the outer cylindrical barrel 12 in which the liquid 20 is enclosed.

In the state shown in FIG. 2, the plunger 18 is also received within the inner cylindrical barrel 14 at the second, open end thereof and is fixated relative to the inner cylindrical barrel 14 as the outwardly protruding, annular projection 102 of the plunger 18 is received within the recess 106 of the inner surface of the outer cylindrical wall 40 of the inner cylindrical barrel 14. The dovetail-like engagement between the projection 102 and the recess 106 allows that the plunger 18 may be displaced into the inner space defined within the inner cylindrical barrel 14, however, is prevented from being retracted from the inner cylindrical barrel 14.

As is evident from FIG. 2, the plunger body 82 is in the state shown in FIG. 2 in registration with the inner space defined within the inner cylindrical wall 42 of the inner cylindrical barrel 14 and consequently in registration with the ampulla 16, however, arranged at a short distance from the rupturable sealing membrane 64 of the ampulla 16 which is locked in the position shown in FIG. 2 by means of the inwardly protruding, annular projections 48, 50, as described above.

The material or medicament 66 enclosed within the ampulla 16 is transferred from the ampulla 16 to the liquid 20 contained within the outer cylindrical barrel 12 by pressing the plunger 18 downwardly into the inner cylindrical barrel 14 from the position or state shown in FIG. 2 to the position or state shown in FIG. 3. As the plunger 18 is moved downwardly, the cutter means 86 perforates the rupturable sealing membrane 64 and presses the entire ampulla 16 downwardly from its position shown in FIG. 2 to the position shown in FIG. 3, i.e. beyond the inwardly protruding, annular projection 48 so as to bring the rupturable, sealing membrane 62 into contact with the cutter means 52 in order to perforate the membrane 62 so as to allow the material or medicament 66 to be expelled from the ampulla 16 to the liquid 20.

As the plunger 18 is pressed downwardly from the position or state shown in FIG. 2 to the position or state shown in FIG. 3, excess air enclosed within the outer peripheral plunger wall 80 of the plunger 18 and within the outer cylindrical wall 40 of the inner cylindrical barrel 14 is vented through the through-going holes 98, the activated carbon filling 90 contained within the filter container 88 and through the apertures 94. The inner space defined within the inner cylindrical wall 42 of the inner cylindrical barrel 14 is also vented through the through-going holes 96, the combined hydrophobic filter and micropore fibre filter 100, the activated carbon filling 90 contained within the plunger body 82 and through the holes 94. Thus, any aerosols or gases liberated from the material or medicament 66, e.g. as the material or medicament is brought into contact with the liquid 20 is vented to the atmosphere, however, filtered through the combined hydrophobic filter and micropore fibre filter 100 and the activated carbon filling 90 so as to eliminate any risk that the person operating the two-compartment syringe assembly 10 is exposed to hazardous aerosols or gases.

After the material or medicament 66 is expelled from the ampulla 10 and transferred to the liquid 20, a dilution of the material or medicament within the liquid 20 is obtained by shaking the two-compartment syringe assembly 10. Provided the outer cylindrical barrel 12 is manufactured from a material which is at least partly transparent or alternatively provided with a transparent window, the person operating the two-compartment syringe assembly 10 may monitor the preparation of the dilution of the material or medicament within the liquid. Provided the dilution is properly prepared, an injection may be performed by means of the two-compartment syringe assembly 10.

It is to be emphasized that the outwardly protruding, annular projection 104 of the outer peripheral plunger wall 80 of the plunger 18 locks within the recess 106 of the inner cylindrical surface of the outer cylindrical wall 40 of the inner cylindrical barrel 14 and prevents the plunger 18 from being retracted from the position shown in FIG. 3.

By pressing the inner cylindrical barrel 14 into the outer cylindrical barrel 12 from the position or state shown in FIG. 3 to the position or state shown in FIG. 4, the liquid 20 having therein the material or medicament diluted is expelled or dispensed from the compartment defined within the outer cylindrical barrel 12 through the nozzle 28 and further through the elongated needle 34 of the needle assembly 30. The excess air present above the surface of the liquid 20 shown in FIG. 3 is vented through the combined hydrophobic filter and micropore fibre filter 100 and the activated carbon filling 90 to the atmosphere. As the inner cylindrical barrel 12 is moved from the position or state shown in FIG. 3, the outwardly protruding, annular projection 54 is disengaged from its engagement within the recess 38 allowing that the inner cylindrical barrel 14 is displaced into the inner compartment defined within the outer cylindrical barrel 12.

In the position or state shown in FIG. 4, the inner cylindrical barrel 14 is locked relative to the outer cylindrical barrel 12 as the outwardly protruding, annular projection 56 locks within the recess 38 of the inner surface of the cylindrical wall 22 of the outer cylindrical barrel 12 and prevents the inner cylindrical barrel 14 from being retracted from its position totally received within the inner compartment defined within the outer cylindrical barrel 12. Consequently, reuse of the two-compartment syringe assembly and separation of the inner cylindrical barrel 14 from the outer cylindrical barrel is prevented. Similarly, the plunger 18 is blocked from being retracted from the inner cylindrical barrel 14 as discussed above and from being separated therefrom.

In FIG. 5, a second embodiment of the two-compartment syringe assembly according to the present invention is shown, designated the reference numeral 110 in its entirety. The second embodiment 110 of the two-compartment syringe assembly according to the present invention differs from the first, presently preferred embodiment 10 of the two-compartment syringe assembly according to the present invention discussed above with reference to FIGS. 1–4 in that the cutter means 52 of the inner cylindrical barrel 14 and the cutter means 86 of the plunger 18 are substituted by perforating means of a different configuration.

Furthermore, the needle assembly 30 shown in FIGS. 2–4 is omitted, as the outer cylindrical barrel 12 of the two-compartment syringe assembly 110 shown in FIG. 5 is provided with a connector for connecting the two-compartment syringe assembly to an infusion bottle or infusion set. The connector comprises a central needle 112, which extends through the spout or nozzle 28 and is blocked at its outer, distal end in the state of storing the two-compartment syringe assembly and of preparing the dilution of the material or medicament 66 within the liquid 20 by means of a plug 114 which is biased outwardly by means of a helical coil 116. The assembly comprising the needle 112, the plug 114, and the coil 116 is protected by a circumferential wall 118 of the outer cylindrical barrel 12.

As an infusion bottle such as a bottle 120 shown in FIG. 5 is connected to the two-compartment syringe assembly 110, a connector plug 122 of the infusion bottle is brought into contact with the needle 112 by forcing the plug 114 upwardly or rearwardly relative to the needle 112 against the biasing force generated by the helical coil 116. After the dilution of the material 66 within the liquid 20 has been dispensed from the two-compartment syringe assembly 110 to the infusion bottle 120, the infusion bottle 120 is removed from the two-compartment syringe assembly 110 which is thereupon disposed and destructed, e.g. in a high-temperature combustion oven of a hospital or the like. The connector plug 122 seals the infusion bottle 120 as the needle 112 is retracted from the infusion bottle.

The plug 114 serves the additional purpose of blocking the outer end of the needle 112 as the infusion bottle 120 is removed from the two-compartment syringe assembly in order to prevent that a person operating the two-compartment syringe assembly, such as a doctor, a nurse or a pharmacist unintentionally contacts the odd end of the needle 112, which might cause serious injuries to the person, as the material or medicament 66 is often extremely toxic or carcinogenic, as the material or medicament 66 may constitute a cytostatic, an antibiotic, a hormone, or a central nervous agent or the like.

The cutter means 52 shown in FIGS. 1–4 is substituted by an openable four-segment cutter 124 which is shown in greater details in FIG. 5a. The four-segment cutter 124 comprises four separate, integrally cast segments, one of which is designated the reference numeral 126 which is provided with a sharp cutting edge 128 and is connected to an adjacent segment through a breakable material strip 130. The four-segment cutter 124 functions as a collapsible cutter means as the cutting edges 128 of the separate segments 126 initially perforate the rupturable, sealing membrane 62 of the ampulla 16, as the ampulla 16 is forced downwardly into contact with the four-segment cutter 124, whereupon the four segments 126 are mutually separated along the material strips 130 and caused to hinge at the base of the individual segment 126 at the wall of the bore 46, as the material or medicament 66 is forced outwardly from the ampulla 16.

The cutter means 86 shown in FIGS. 1–4 of the plunger 18 is substituted by a protruding tip 132 which is provided centrally at the end wall of the central plunger body 82 of the plunger 18. The protruding tip 132 is circumferentially encircled by the through-going holes 96. As the plunger 18 is forced into the inner cylindrical barrel 12, the plunger body 82 initially forces the ampulla 16 downwardly into contact with the four-segment cutter 124, as the central plunger body 82 contacts an inner wall of an annular fixation ring 134 which prevents the membrane 64 from getting into contact with the perforating protruding tip 132. The ampulla 16 is in the second embodiment 110 of the two-compartment syringe assembly according to the present invention shown in FIG. 5 maintained in a frictional surface contact established between the outer peripheral surface of the glass tube of the ampulla 16 and the inner cylindrical surface of the inner cylindrical wall 42 of the inner cylindrical barrel 14. As the plunger 18 is forced downwardly, the annular fixation ring 134 initially forces the ampulla 16 downwardly, as discussed above, into an end position in which the lower rim of the glass tube 6 of the ampulla 16 rests behind the recess defined behind the bore 46, and further advancement of the plunger 18 causes the plunger body 82 to be forced through the annular fixation ring 134 so as to force the protruding tip 132 of the central plunger body 82 into contact with the rupturable sealing membrane 64 of the ampulla 16 for perforating the membrane and for forcing the material or medicament 66 contained within the ampulla 16 out from the compartment defined within the ampulla 16 and down into the liquid 20.

It is to be realized that the plunger body 82 in the second embodiment 110 shown in FIG. 5, and also in the first embodiment 10 shown in FIGS. 1-4, provides a close fit within the cylindrical glass tube of the ampulla 16 in order to, to any substantial extent, cause any material adhering to the inner surface of the glass tube 60 of the ampulla 16 to be forced out of the ampulla 16 as the plunger body 82 is urged into the ampulla 16.

In FIG. 6a–6e, a process of filling the ampulla 16 of the two-compartment syringe assembly is shown. In FIG. 6a, the glass tube 60 is shown cut from a length of a glass tube.

In FIG. 6b, the rupturable, sealing membrane 62 is applied to the first end of the glass tube 60, e.g. by welding or by glueing the membrane 62 to the lower end of the glass tube.

In FIG. 6c, the material 66 is filled into the chamber or compartment defined within the glass tube 60 by means of a dispensing nozzle 142 in a predetermined exact amount, such as an amount of the order of 3–5 ml.

In FIG. 6d, the rupturable, sealing membrane 64 is applied to the opposite second end of the glass tube 60 for sealing the chamber or compartment defined within the glass tube 60 of the ampulla 16. The production steps carried out in accordance with FIG. 6c and FIG. 6d may be carried out in a sterilized, evacuated chamber, provided the material calls for such precautions.

After the ampulla 16 has been sealed, the entire ampulla may be sterilized in a sterilizing chamber 140 shown in FIG. 6c by exposure to high-temperature treatment or high-frequency treatment, such as exposure to high-temperature steam, UV, IR or microwave radiation or the like.

In FIG. 7a–7e, a process of producing the two-compartment syringe assembly according to the present invention is shown. In FIG. 7a, the outer cylindrical barrel 12 and the inner cylindrical barrel 14 are assembled by positioning the inner cylindrical barrel 14 in the extracted position or state shown in FIGS. 1, 2, 3, and 5.

In FIG. 7b, the liquid 20 which may constitute a solvent, such as an aqueous or alcoholic suspension of e.g. sugar, an acid, or a base, an electrolytic solution or the like, is dispensed from a dispensing nozzle 144 through the central passage defined within the inner cylindrical wall 40 of the inner cylindrical barrel 14.

In FIG. 7c, the sterilized ampulla 16 is introduced into the inner cylindrical barrel 14 through the upper open end thereof.

In FIG. 7d, the plunger 18 is mounted as the lower first end of the plunger 18 is introduced through the upper, open end of the inner cylindrical barrel 14. The plunger is locked in the position or state shown in FIGS. 1, 2, and 5. After the entire two-compartment syringe assembly 110 has been assembled, the two-compartment syringe assembly may be sterilized, e.g. in the sterilizing chamber 140 shown in FIG. 6e.

In FIG. 7e, the assembled two-compartment syringe assembly, optionally sterilized, is encapsulated within a sealed plastic bag 160. After encapsulating the assembled two-compartment syringe assembly, optionally sterilized, the plastic bag 160 and the two-compartment syringe assembly 110 contained within the sealed plastic bag may be sterilized, e.g. in the sterilizing chamber 140 shown in FIG. 6e, or in a different sterilizing chamber or in accordance with a different sterilizing technique.

It is to be realized that the ampulla 16 may be integrated into the inner cylindrical barrel 14 of the two-compartment syringe assembly which, of course, calls for certain minor modifications of the above described processes of producing the ampulla and the two-compartment syringe assembly. Instead of producing a separate ampulla 16 as shown in FIG. 6a–6e, the entire inner cylindrical barrel 14 is manufactured in accordance with the technique disclosed in FIG. 6a–6e, as the inner compartment defined within the inner cylindrical wall 40 of the inner cylindrical barrel 14 is provided with the membrane 62 at the first, lower end of the inner cylindrical barrel 14, whereupon the material or medicament 66 is introduced into the inner compartment defined within the inner cylindrical barrel 14 by means of the dispensing nozzle 142. In a step corresponding to the step shown in FIG. 6d, the membrane 64 is applied to the upper, second end of the inner cylindrical barrel for sealing the inner compartment defined within the inner cylindrical wall 40 of the inner cylindrical barrel 14.

Similarly, the step shown in FIG. 7a is deleted as the liquid or solvent is dispensed from the dispensing nozzle 144 into the inner compartment defined within the outer cylindrical barrel 12 prior to the step of assembling the outer cylindrical barrel 12 and the inner cylindrical barrel 14 integrally containing the material or medicament in the inner compartment defined within the inner cylindrical barrel 14.

EXAMPLE 1

A prototype implementation of the first, preferred embodiment of the two-compartment syringe assembly according to the present invention shown in FIGS. 1–4 and discussed above with reference thereto was made from the following components:

The outer cylindrical barrel 12 was made from HDPE and had the following dimensions. The outer diameter of the cylindrical barrel was 35 mm, the inner diameter of the cylindrical barrel was 32 mm. The inner height of the barrel was 60 mm. The outer diameter of the circumferential flange 26 was 55 mm, and the thickness of the wall of the circumferential flange 26 was 2 mm.

The inner cylindrical barrel 14 was made from HDPE and had the following dimensions. The overall length of the barrel was 78 mm, the outer diameter of the barrel was 32 mm, the inner diameter of the outer cylindrical wall of the barrel was 30 mm, the length of the inner cylindrical wall was 60 mm. The outer diameter of the inner cylindrical wall was 15 mm. The inner diameter of the inner cylindrical wall was 13 mm. The outer diameter of the annular flange was 38 mm. The thickness of the wall of the annular flange was 2 mm.

The ampulla 16 was made from a cylindrical glass tube of an outer diameter of 13 mm and of a wall thickness of 1 mm. The membranes were made from a laminated foil assembly comprising a 30 μm PE foil applied in contact with the rim of the glass tube and sealed thereto in a welding process, and a 30 μm aluminum foil. The welding process was carried out by means of a pressing tool heated to a temperature of the order of 150° C.–200° C. which generated an excess pressure of the order of 500 g—1.5 kg for pressing the foil assembly towards the rim of the glass tube for a period of time of the order of 0.5–1 sec. The welding process was carried out manually, during which welding process the adhesion of the laminated foil assembly to the rim of the glass tube was first tested to mechanical adherence and visually monitored.

The plunger 18 was made from HDPE. The outer diameter of the outer peripheral plunger wall was 30 mm. The wall thickness of the outer peripheral plunger wall was 0.8 mm, the height of the outer peripheral plunger wall was 57 mm, and the end of the central plunger body was protruding 3.5 mm beyond the outer lower or opened end of the plunger. The outer diameter of the plunger body was 12 mm. The container of the plunger defined in the inner container had a diameter of 20 mm and a container height of 16 mm. The plug sealing the filter container had corresponding dimensions and was integrally cast having a wall thickness of 0.8 mm.

The two-compartment syringe assembly was tested as the outer cylindrical barrel 12 was filled with water, and ampullas containing NaCl and dye Green S-E 142 were manufactured. The rupturable sealing membranes of the individual ampulla were easily ruptured as the two-compartment syringe assembly was operated as discussed above with reference to FIGS. 2–4.

EXAMPLE 2

The inner cylindrical barrel and the plunger of the two-compartment syringe assembly may alternatively be cast in a two-step casting process in which the cylindrical walls of the inner cylindrical barrel and the plunger are cast from HDPE, whereupon in a second, integral casting step, O-ring sealings are cast from a more elastic thermoplastic material, such as LDPE or LLDPE substituting the outwardly protruding annular projections of the inner cylindrical barrel and the plunger.

EXAMPLE 3

Materials which may be of interest and relevance in connection with the two-compartment syringe assembly are: The outer cylindrical barrel, the inner cylindrical barrel, and the plunger may be cast a thermoplastic material, e.g. polystyrene, polyimide, polycarbonate, polymethacrylates, polyvinylidenefluoride, polyamide, polyvinyl alcohol, and preferably polyolefines, such as low-density polyethylene (LDPE), medium-density polyethylene (MDPE), high-density polyethylene (HDPE), linear low-density polyethylene (LLDPE), polypropylene (PP), polypropylene-ethylene-copolymer, or any mixture thereof. The inner cylindrical wall of the inner cylindrical barrel may optionally be plasma-coated in order to provide barrier properties by electron-ray-treatment, corona-treatment, plasma-treatment, plasma-polymerisation or any other appropriate surface-treatment, for providing an integral ampulla of the inner cylindrical barrel of high-resistance, high-storage capability. The rupturable sealing membranes may be made from aluminum, laminated aluminum, such as 30 µm aluminum, which is glued and/or welded to the rim of the inner compartment defined within the inner cylindrical barrel or defined by the glass tube of the ampulla. Alternatively, LDPE, PETP, or PU, optionally covered by a laminated aluminum foil, such as 30 µm LDPE, 12 µm PETP, 12 µm Al, 80 µm LDPE, may be used. Alternative laminated foil structures may be made from HIPS (high-impact polystyrene), PVOH (polyvinyl alcohol) constituting a 100% air-tight barrier in dry state, and HIPS, alternatively LDPE or PP, PVOH, and HIPS or PP, or further alternatively HDPE, PVOH, and HDPE. Another interesting and relevant foil material is PIMSP (polytrimethylsilylpropylene).

Although the two-compartment syringe assembly and the method of producing a two-compartment syringe assembly integrally containing a solvent and a material or medicament to be dissolved in the solvent has been described with reference to specific, preferred embodiments, numerous modifications are perceivable by a person having ordinary skill in the art within the inventive concept of the present invention as defined in the appended patent claims. Such obvious modifications and alterations of the present invention are to be construed part of the present invention.

LIST OF REFERENCES 10 first embodiment of two-compartment syringe assembly
12 first or outer cylindrical barrel
14 second or inner cylindrical barrel
16 ampulla
18 plunger
20 liquid or solvent
22 cylindrical wall
24 first end or dispensing end
26 circumferential flange
28 spout or nozzle
30 needle assembly
32 fixation component
34 needle
36 annular flange
38 recess
40 outer cylindrical wall
42 inner cylindrical wall
44 end wall
46 central, through-going hole
48 inwardly protruding, annular projection
50 inwardly protruding, annular projection
52 cutter means
54 outwardly protruding annular projection
56 outwardly protruding annular projection
60 cylindrical glass tube
62 rupturable, sealing membrane
64 rupturable, sealing membrane
66 material or medicament
68 circumferential score line
70 central part
72 radial score line
80 outer peripheral plunger wall
82 central plunger body
84 end wall
86 cutter means
88 filter container
90 activated carbon filling
92 plug body
94 venting hole
96 through-going hole
98 through-going hole
100 combined hydrophobic filter and micropore fibre filter
102 outwardly protruding, annular projection
104 outwardly protruding, annular projection
106 recess
110 second embodiment of two-compartment syringe assembly
112 central needle
114 plug
116 helical coil
118 circumferential wall 120 infusion bottle
122 connector plug
124 four-segment cutter
126 segment
128 cutting edge
130 material strip
132 protruding tip
134 annular fixation ring
140 sterilizing chamber
142 dispensing nozzle
144 dispensing nozzle
160 sealed plastic package

What is claimed is:

1. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, and said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof.

2. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received within said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and said plunger defining a venting passage extending through said plunger body, and further comprising a filtering means, said filtering means being arranged in and enclosed within said venting passage.

3. The two-compartment syringe assembly according to claim 2, said filtering means comprising a hydrophobic filter means.

4. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received within said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, and said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and further comprising a first, breakable locking means for locking said plunger in said first, extracted position relative to said second cylindrical barrel.

5. The two-compartment syringe assembly according to claim 4, further comprising a second locking means for locking said plunger in said second, inserted position relative to said second cylindrical barrel when displaced to said second, inserted position from said first, extracted position and for preventing said plunger from being retracted from said second, inserted position relative to said second cylindrical barrel.

6. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall and defining a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received within said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, and said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and further comprising a third, breakable locking means for locking said second cylindrical barrel in said third, extracted position relative to said first cylindrical barrel.

7. The two-compartment syringe assembly according to claim 1, further comprising a fourth locking means for locking said second cylindrical barrel in said fourth position relative to said first cylindrical barrel when displaced to said fourth position from said third, extracted position and for preventing said second cylindrical barrel from being retracted from said fourth position relative to said first cylindrical barrel.

8. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, said second cylindrical barrel being composed of an outer body part and a capsule part, said capsule part comprising said inner cylindrical wall and said rupturable seals, and said outer body part constituting a support structure having a central recess in which said capsule part is received.

9. The two-compartment syringe assembly according to claim 8, said capsule part constituting a prefilled, sterilized ampulla.

10. The two-compartment syringe assembly according to claim 9, said capsule part comprising a cylindrical glass tube having opposite ends at which said rupturable seals are fixated relative to said cylindrical glass tube.

11. The two-compartment syringe assembly according to claim 10, said rupturable seals being made from a foil of a plastic material.

12. The two-compartment syringe assembly according to claim 11, said rupturable seals being provided with score lines.

13. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and said first cylindrical barrel being made from a thermoplastic material.

14. The two-compartment syringe assembly according to claim 13, said the second cylindrical barrel being made from a thermoplastic material.

15. The two-compartment syringe assembly according to claim 14 said inner cylindrical wall of said second cylindrical barrel being made from a material which has been surface-treated in order to provide barrier properties by electron-ray-treatment, corona-treatment, plasma-treatment, plasma-polymerisation or any other appropriate surface-treatment.

16. The two-compartment syringe assembly according to claim 13 said plunger being made from a thermoplastic material.

17. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and said rupturable seals being made from a foil of a plastic material.

18. The two-compartment syringe assembly according to claim 17, said rupturable seals being provided with score lines.

19. A two-compartment syringe assembly for storing a liquid and a material and for preparing a dilution of said material within said liquid prior to dispensing said liquid, comprising:

a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, a plunger having a central plunger body and an outer peripheral plunger wall circumferentially encircling said central plunger body, said liquid being received within said first compartment of said first cylindrical barrel, said material being enclosed within said second compartment of said second cylindrical barrel, said plunger being inserted into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, said plunger being axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, said second cylindrical barrel being inserted into said first cylindrical barrel through said second end thereof, having its first end received within said first compartment, said second cylindrical barrel being axially displaceable relative to said first cylindrical barrel in sealing relationship therewith from a third, extracted position to a fourth position in which said first compartment is substantially diminished and said liquid is dispensed from said first cylindrical barrel through said first end thereof, and said material being a highly active or aggressive material.

20. The two-compartment syringe assembly according to claim 19, said liquid being a solvent, an alcoholic or aqueous solution, base, acid, saline or sugary solution or the like, or any combination thereof.

21. A method of producing a two-compartment syringe assembly for storing a liquid and a material and for preparing a dilution of said material within said liquid prior to dispensing said liquid, comprising the steps of providing a first cylindrical barrel having a first cylindrical wall and defining a first and a second end of said first cylindrical barrel, a first compartment being defined within said first cylindrical barrel by said first cylindrical wall, said first end of said first cylindrical barrel constituting a dispensing end and said second end of said first cylindrical barrel being open, providing a second cylindrical barrel having an outer cylindrical wall, an inner cylindrical wall, and an end wall, and having a first and a second end, said outer and inner cylindrical walls being integrally connected through said end wall at said first end of said second cylindrical barrel, a second compartment being defined within said second cylindrical barrel by said inner cylindrical wall of said second cylindrical barrel and constituting a sealed compartment sealed by rupturable seals provided at said first and second ends of said second cylindrical barrel, providing a plunger having a central plunger body and an outer peripheral plunger wall circumferentially encircling said central plunger body, arranging said liquid being received within said first compartment of said first cylindrical barrel, arranging said material being enclosed within said second compartment of said second cylindrical barrel, inserting said plunger into said second cylindrical barrel through said second end thereof, having its plunger body registered relative to said inner cylindrical wall of said second cylindrical barrel, and having its outer peripheral plunger wall received between said inner cylindrical wall and said outer cylindrical wall of said second cylindrical barrel, so that said plunger is axially displaceable relative to said second cylindrical barrel from a first, extracted position to a second, inserted position in which said plunger body of said plunger is inserted into said second compartment of said second cylindrical barrel through said second end thereof, having ruptured said rupturable seals at said first and second ends of said second cylindrical barrel, and establishes a sealing relationship with said inner cylindrical wall of said second cylindrical barrel, so as to allow said material to be dispensed from said second compartment to said first compartment for being diluted within said liquid, and inserting said second cylindrical barrel into said first cylindrical barrel through said second end thereof, having its first end received within said first compartment, so that said second cylindrical barrel is axially displaceable relative to said first cylindrical barrel in sealing relationship therewith from a third, extracted position to a fourth position in which said first compartment is substantially diminished and said liquid is dispensed from said first cylindrical barrel through said first end thereof.

* * * * *